United States Patent [19]

Claypool et al.

[11] Patent Number: 4,672,200
[45] Date of Patent: Jun. 9, 1987

[54] OPTICAL INSPECTION OF TRANSPARENT LAYERS

[75] Inventors: Mark P. Claypool, Horseheads; Patrick T. Battersby, Elmira, both of N.Y.

[73] Assignee: Emhart Industries, Inc., Farmington, Conn.

[21] Appl. No.: 795,376

[22] Filed: Nov. 5, 1985

[51] Int. Cl.⁴ .............................................. H01J 5/16
[52] U.S. Cl. .................. 250/227; 250/223 B; 350/240; 350/445
[58] Field of Search .................. 250/223 B, 227; 356/239, 240, 445, 448

[56] References Cited

U.S. PATENT DOCUMENTS

| | | | |
|---|---|---|---|
| 3,327,584 | 6/1967 | Kissinger | 88/14 |
| 3,771,873 | 11/1973 | Tourret | 250/227 X |
| 3,940,608 | 2/1976 | Kissinger et al. | 250/227 |
| 4,539,474 | 9/1985 | Takahata | 250/227 X |

FOREIGN PATENT DOCUMENTS 1376304 12/1974 United Kingdom ................ 250/227

OTHER PUBLICATIONS

Kissinger et al., "Improved Noncontact Fibre Optics/Lens Displacement Measuring System", 1973.
Kissinger, "Fibre Optic Lever Displacement Sensors and Automated Reflectance Compensation Improvements", 1983, FOC/LAN.
Cook et al., "Fibre Optic Lever Displacement Transducer", 1979, Applied Optics vol. 18, No. 19 pp. 3230-3241.

Primary Examiner—Eugene R. LaRoche
Assistant Examiner—James C. Lee
Attorney, Agent, or Firm—Arthur B. Moore; Arthur J. Samodovitz

[57] ABSTRACT

Method and apparatus for optical inspection of transparent layers such as the wall of glass and plastic containers, using bifurcated fiber optic probes. One or more of such fiber optic probes are directed at the wall of a transparent container, and light emitted thereby is selectively reflected from both the inner and outer surfaces of the container wall. Each probe includes a pair of bifurcated fiber optic bundles which are disposed at different distances behind a 1:1 lens system, resulting in two focal points at different distances from the fiber optic probe. Relative motion of the inner and outer wall surfaces between these focal points results in measurable variations of the probe output signals, which variations may be interpreted to track wall thickness and concentricity. An alternative detection scheme uses a probe with a single bifurcated bundle, and reciprocates such probe relative to the container wall while measuring the separation of null points of the output signal.

19 Claims, 7 Drawing Figures

OPTICAL INSPECTION OF TRANSPARENT LAYERS

BACKGROUND OF THE INVENTION

The present invention relates to optical inspection of glassware containers and like translucent articles, and more particularly to optical inspection methods and apparatus for dimensional gauging of wall thickness and concentricity. The invention further relates to glassware inspection using fiber optic devices.

Thinwall detection is a critical type of dimensional gauging for glassware articles, inasmuch as thin areas within the walls of glass containers render the containers susceptible to breakage upon impact or pressurized filling. Most present inspection techniques for glass container thickness rely on contacting the container wall with capacitive detector probes. Sensitive electronic circuits measure frequency changes generated by the varying dielectric of glass as a capacitive element of the circuit. Such devices may employ linear probes which contact rolling containers, or may space the probe from the sidewall by a fixed distance during rotation.

Such capacitive measurement devices suffer several significant drawbacks. These devices do not perform well at high speeds of container rotation, at which the tracking head will not remain in stable engagement with the surface. When such tracking heads disengage the container sidewall, false thickness readings can occur. Such contact devices cannot effectively measure thickness at the container seams, and generally utilize a masking scheme in the electronics to ignore readings at or near the seams. This is unfortunate as thinwall distribution is often found at container seams. These contact devices are generally not well suited to measuring wall thickness at or near the heel or shoulder areas of containers. Furthermore, these prior art devices are subject to severe wear, and may cause scratching, chipping, or abrasion of container surfaces. Finally, this prior art technique is unsuitable for thinwall gauging of plastic containers, which are generally flexible and deform under the contact forces.

Thickness inspection has also played a significant role in other glass manufacturing processes, such as flat glass or transparent plastic sheet manufacture.

Contact inspection techniques have predominated as well in "out-of-round" measurements for glassware containers. One such prior art technique relies upon a spring or air loaded probe to track the container. Other commercial approaches include limit switches, and a combination of a mechanical tracking device defining a window with a laser beam directed through the window. Such mechanical approaches suffer many of the drawbacks recited above for prior art thinwall detectors.

U.S. Pat. No. 4,476,533 to Dandt et al. discloses an optical inspection system to be employed at the "hot end" of glassware container production shops. In the Dandt system, fiber optic bundles propogate light beams across the container paths on hot end conveyor lines. A sensing system positioned on the opposite side of the conveyor includes a focusing system and light detection devices. Electronic processing apparatus processes the photodetector outputs to determine various glassware dimensions. Various processing algorithms are disclosed for diameter, perpendicular offset, and roundness.

U.S. Pat. Nos. 3,327,584 to Kissinger and 3,940,608 to Kissinger et al. disclose fiber optic devises which are designed for measuring the proximity of a bifurcated fiber optic probe to a light-reflecting test object. These devices utilize adjacent pairs of light-transmitting and light-receiving fibers—the "fiber optic lever" principle. By the nature of the interaction between the field of illumination of the transmitting fibers, and the field of view of the detector fibers, such devices provide precisely varying output signals (intensity of received light) as a function of the gap between the fiber optic probe and the test surface. The later of these patents discloses the improvement wherein the probe incorporates a lens system to focus the image of the end face of the fiber optic bundle onto the test surface, and to refocus the reflected light onto the bundle end face in an upright relationship. These probes may be used to measure displacement, as well as to measure vibration characteristics, and Kissinger and his collaborators disclose a number of possible applications. Kissinger et al. do not, however, disclose the use of these devices in the detection of wall thickness of transparent containers, nor for concentricity measurements for round articles, either in the above patents or in other publications.

Accordingly, it is a primary object of the invention to provide noncontact inspection devices for the measurement of wall thickness of glassware containers and other transparent articles. Such devices should provide accurate, reliable use, without the mechanical shortcomings typical of contact measuring probes. This apparatus should be usable with containers having a variety of materials, dimensions, and other physical characteristics.

These devices should be capable of thinwall detection at container seams, and at the shoulders and heels.

A further object is to provide an improved technique for concentricity, or "out-of-round" measurement.

Yet another object is to achieve an inspection technique which may be easily adapted to translucent plastic articles.

A still further object is to provide an inspection technique which may be advantageously applied to other applications, such as the manufacturer of flat glass.

SUMMARY OF THE INVENTION

In furthering the above and additional objects, the invention utilizes one or more fiber optic scanning heads directed at a transparent layer (glassware wall, flat glass sheet, etc.), scanning head including two (or, in an alternative embodiment of the invention, one) bifurcated fiber optic bundles together with cooperating optical and electronic components. Each bifurcated fiber optic bundle has sender and receiver bifurcations respectively containing sender and receiver optical fibers, and a joined portion containing both sets of fibers terminating at a probe end. Each fiber optic bundle has a light source for illuminating the sender fibers at an end opposite the probe end, and a photodetector device for producing an output signal representative of the relative intensity of light transmitted by the receiver fibers. The scanning head further includes a lens system which transmits light emitted from the sender fibers at the probe end toward the container wall, where it is partially reflected by nearer and farther surfaces back toward the probe and via the lens system.

Advantageously the photodetector output is processed to derive relative intensity signals representing the intensity of light collected by the receiver fibers over a sampling interval. These relative intensity signals are interpreted to derive the relative locations of the nearer and farther layer surfaces, thereby enabling the tracking of wall thickness and concentricity (out-of-roundness).

In a first, preferred embodiment of the invention the scanning head includes a pair of fiber optic bundles spaced at different distances from the lens system. The lens system focuses light emitted by the nearer fiber optic bundle at relatively distant focal point, while light emitted by the farther bundle is focused at a relatively proximate focal point. The transparent layer is maintained between these two focal points during inspection, and the relative intensity signals produced by the respective fiber optic bundles are both interpreted to derive thickness and concentricity (i.e. layer location) readings. Desirably the processing electronics includes a memory device for correlating relative intensity readings with surface locations for the nearer and farther surfaces.

An alternative embodiment of the invention utilizes a single-bundle scanning head, and reciprocates this head relative to the transparent layer during inspection. The probe output is processed during the cycling of the fiber optic probe to sense first and second nulls in the relative intensity signal. A position sensing device continually senses the position of the scanning head relative to the layer. First and second nulls in the processed probe output are correlated with respective sensed probe positions to determine the surface locations at said first and second peaks. This data may be used to derive wall thickness, or for a container of circular symmetry to track concentricity by rotating the container around its axis of symmetry during inspection. When monitoring a rotating container it is necessary that the cyclical motion of the scanning head be at a relatively high rate with reference to the speed of rotation of the container.

BRIEF DESCRIPTION OF THE DRAWINGS

The above and additional aspects of the invention are illustrated in the following detailed description of the preferred embodiment, which should be taken together with the drawings in which.

DETAILED DESCRIPTION

Figure 1:
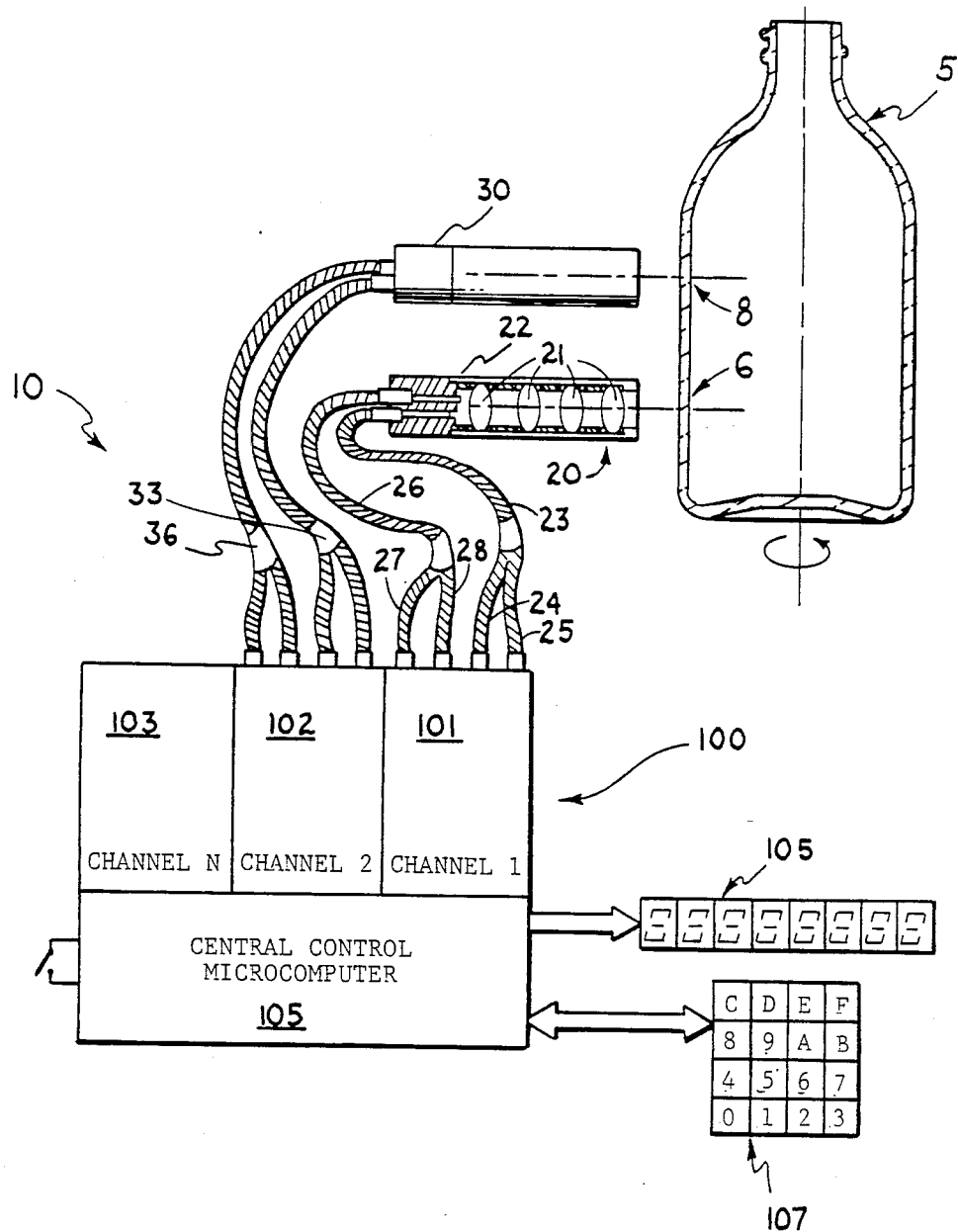
FIG. 1 is a partial, somewhat schematic view of inspection apparatus in a preferred embodiment of the invention.

The present invention makes use of the fiber optic lever principle, which is known in the prior art for displacement transducers, and extends this to the measurement of wall thickness and concentricity in translucent containers and the like. The technique of the insertion is disclosed below in the context of inspection of glassware containers, but is equally applicable to other inspection applications involving transparent layers, such as flat glass manufacture. FIG. 1 illustrates the construction of an inspection device 10 in accordance with a preferred embodiment of the invention. Inspection assembly 10 includes one or more probes (here, two probes 20 and 30 are shown) such probes being trained on the sidewall of translucent container 5 at different elevations thereof. In the illustrated embodiment, container 5 is caused to rotate relative to probes 20 and 30 so that probe 20 performs a complete circumferential scan at elevation 6, and probe 30 at elevation 8. As shown for probe 20, each probe includes a pair of fiber optic bundles 23, 26 with respective bifurcations 24, 25 and 27, 28. Probe 20 further includes a 1:1 lens system having four lenses 21 mounted in holder 22.

Figures 3, 7:
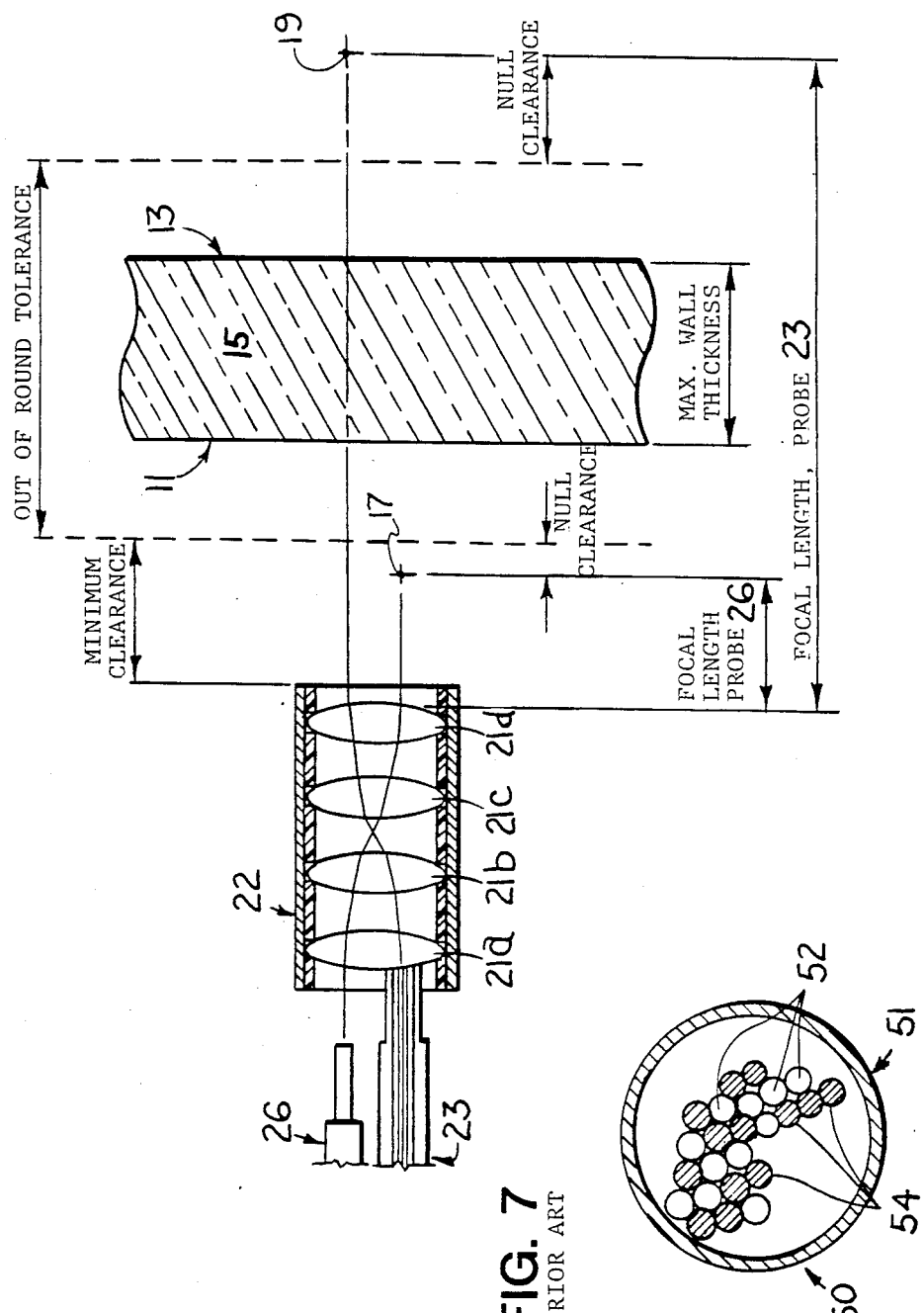
FIG. 3 is a partial schematic view of a given probe from the apparatus of FIG. 1, shown in proximity to the container wall.
FIG. 7 is a plan view of a fiber optic bundle, as seen from an end proximate the probe target.

With reference to FIG. 7, a given optical fiber bundle 50 viewed from the end thereof nearest container 5 includes fibers of a light conducting medium with a light shielding sheath 51. The fiber optic bundle includes light transmitting fibers 52 and light receiving fibers 54, approximately equal in number, thoroughly intermixed in a random distribution.

Referring again to FIG. 1, each probe is associated with a respective channel of the signal processing assembly 100. For example, the channel 1 electronics 101 includes a light source (not shown) for each of transmitter probe bifurcations 24, 27, and a photodetection device (not shown) for each of the receiver bifurcations 25, 28. Channel 1 elements, as dicussed in detail below, further include signal processing elements for deriving digital light intensity signals from the photodetector outputs, and a microprocessor for analyzing the digital light intensity signals to generate reject signals based upon user-defined parameters. Central control microcomputer 105 collects the reject information from the various channel microprocessors and handles operator interface via keyboard 107 and display 105.

It is known from the prior art that a single-bundle system such as that of U.S. Pat. No. 3,940,608 has a single focal point, and that the movement of a reflecting surface toward such focal point will create an out-of-focus image which increases in sharpness. Thus, light will be reflected back toward both sender and receiver fibers generating an increasing signal as the surface moves towards the focal point. When the surface reaches the focal point, the focussed image reflected back to the fibers falls almost exclusively on the transmitting fibers. The photodetector output therefore drops sharply creating a "null" in the light intensity characteristic. As the surface continues through the focal point the signal again peaks and then decreases gradually.

Figure 2:
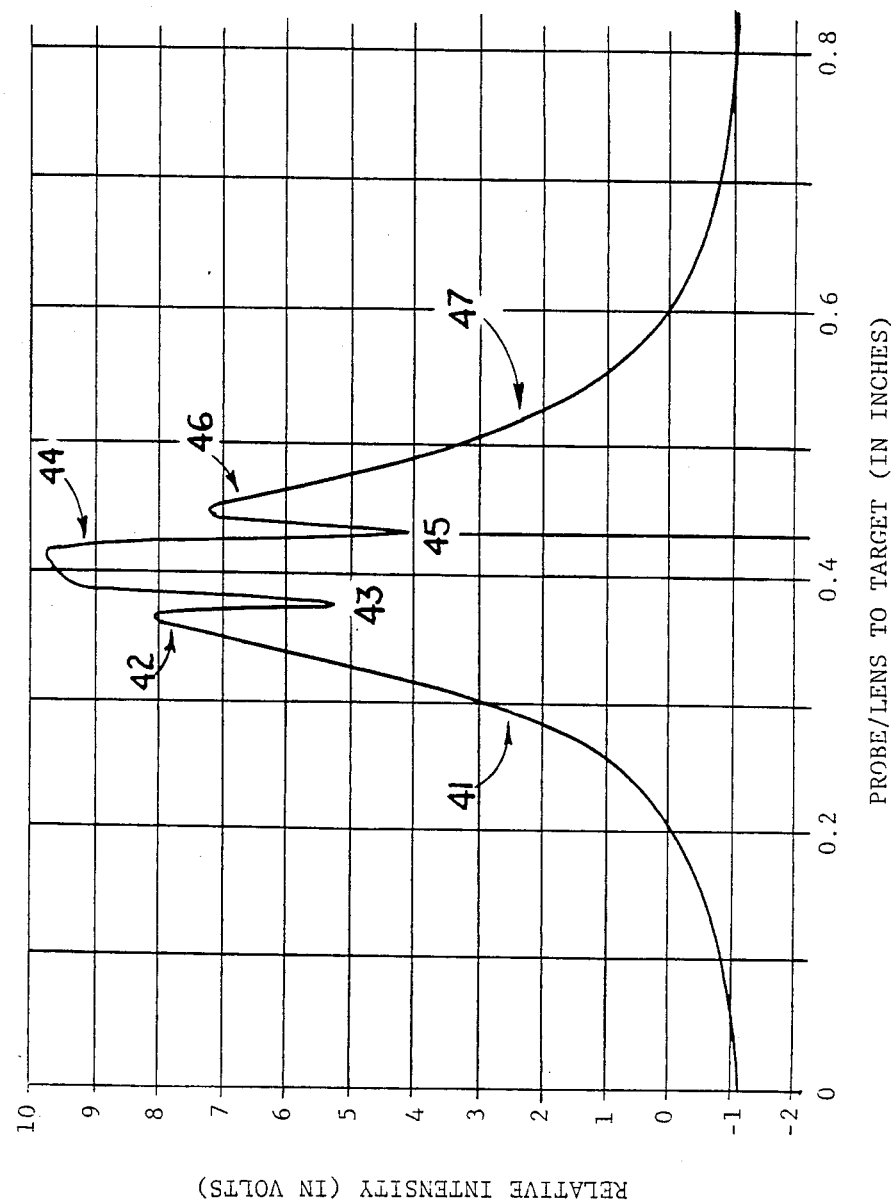
FIG. 2 is a plot of relative intensity (probe output) as a function of probe-to-target distance, for a given single-bundle probe used to scan a glass container wall.

The present invention exploits the optical properties of a translucent body having inner and outer surfaces, such as the sidewall of a translucent container. Light impinging on such articles will be partially reflected by the outer surface, and partially reflected by the inner surface. FIG. 2 is a graph of "relative intensity" as measured by a photodetector of a single-probe system (such as the scanning head 120 of FIG. 6), over varying separations of the probe from the first (closer to probe) surface of the transparent wall. Examining the intensity curve from right to left, in segment 47 (the "front slope") as the gap decreases the intensity measurement increases to a first peak 46. Then, when the first surface reaches the image focal point a signal null 45 occurs. As the first surface continues past the focal point, another, higher peak 44 is reached; peak 44 is higher than peak 46 because it represents the sum of received reflections from both the inner and outer surfaces. A second null 43 occurs when the second (farther) surface of the transparent article appears to the system to have reached the image focal point. The focal point for null 43 has shifted, however, because of the refraction of light passing from air into the transparent medium 15. As the focussed image goes beyond the second surface another peak 42 occurs and the curve gradually decreases at 41 (the "back slope") as the image becomes increasingly blurred, until the first surface contacts the probe lens.

The apparatus of FIG. 6, discussed below, derives the thickness between container surfaces 11 and 13 by measuring the distance between nulls 43 and 45 (FIG. 2), using the known index of refraction of transparent medium 15. However, this alternative embodiment of the invention achieves a low degree of resolution in the inspection of containers processed at typical production cycle speeds, and for this reason the embodiment of FIGS. 1, 3–5 is considered the most preferred embodiment of the invention. As best seen in FIG. 3 this inspection scheme makes use of a pair of bifurcated fiber optic bundles 23, 26 for a given inspection head 20. Bundles 23 and 26 are located at different distances behind 1:1 lens system 21, resulting in respective focal points 19 and 17 of different focal lengths (the focal point 19 for the nearer probe 23 is further from the inspection head 20). Inspection head 20 is designed in relationship to the expected thickness and location of transparent wall 20 during scanning so that this wall will remain positioned within an interval between focal points 17 and 19 (labelled as the "out of round tolerance" segment in FIG. 3). As further explained below, this geometric arrangement ensures that fiber bundle 23 will sense reflections along the back slope of its output characteristic, while bundle 26 senses reflections along the front slope of its output curve.

Probe 20 should be aligned so it is reasonably perpendicular to the associated wall surface in order to provide satisfactory reflectance. Preferably, each probe should be oriented within ten degrees from perpendicular. This requirement does not prevent the use of the inspection techniques of the present invention to examine contoured container walls, shoulders, heels etc. as long as this perpendicularity is maintained.

The technique of the preferred embodiment (FIGS. 1, 3 and 5) takes advantage of an empirically observed phenomenon which has been found to hold true over a variety of transparent materials 15 and configurations of lens system 21. That is, the relative intensity values along both the front and back slopes of the output characteristic will vary as a percentage of the respective peak value in a manner which may be correlated with the distance of the inspection head 20 from the surface causing the relection. As the transparent wall 15 moves closer to the probe 20, the signal from bundle 26 will increase along its front slope, while the signal from bundle 23 will decrease along its back slope. Conversely, the motion of wall 15 away from probe 20 will cause the signal from bundle 26 to decrease along its front slope and the signal from bundle 23 to increase along its back slope.

Figure 4:
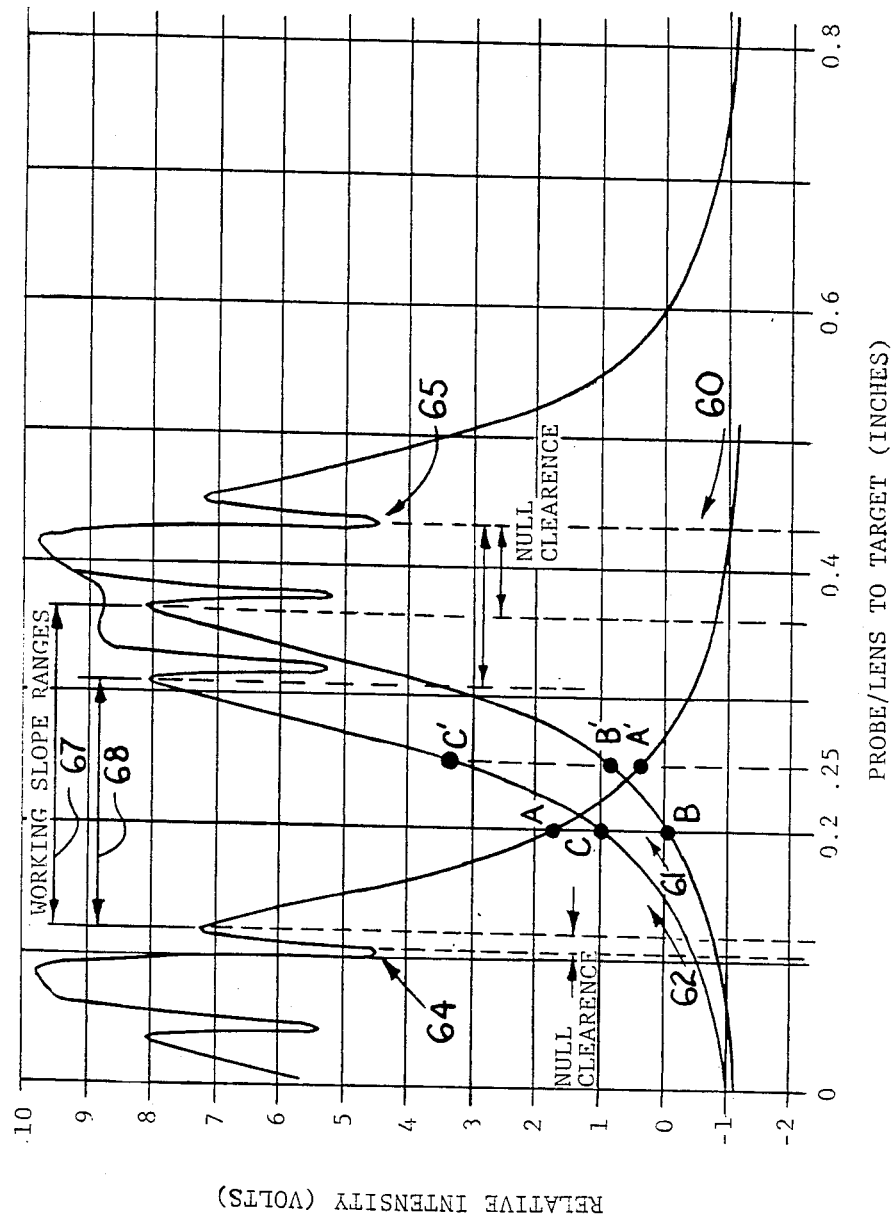
FIG. 4 is a plot of relative intensity (probe output) as a function of probe-to-target distance, for a given dual-bundle probe used to scan a glass container wall.

FIG. 4 provides a quantitative example of the operation of the apparatus of FIG. 3 in the measurement of wall thickness and out-of-roundness (local wall displacement). Curve 60 represents the output characteristic from sensor 26 (used to track the first surface 11); Curve 61 the output characteristic of probe 23 (second surface probe) for a wall thickness of 0.086 inches; and curve 62 the output characteristic of sensor 23 for a wall thickness of 0.170 inches. Points A, B, and C represent relative output readings taken when the first surface 11 is located 0.20 inch from probe 20, while A', B', and C' are readings taken at a probe-first surface distance of 0.25 inch.

In the illustrated example, it will be seen that for a first surface distance of 0.20 inch the relative output at intersect point A for curve 60 (sensor 26) is 1.7 volts while the point B value (sensor 23, 0.086 wall thickness) is −0.15 volt. If the wall thickness increases to 0.170" while the first surface distance remains the same, it will be seen that the output C of sensor 23 increases to around 1.0 volt. In general, the relative output of the second surface sensor increases with greater wall thickness if the probe-to-first surface distance remains constant. Thus, as a second example, C' represents a higher relative output value than B' (i.e. an increasing second surface probe output with increasing wall thickness).

FIG. 4 also illustrates the quantitative effect of out-of-round shifting. Thus for a given wall thickness of 0.086 inches, if the first surface-to-probe distance increases from 0.20 inch to 0.25 inch, the output of sensor 26 will decrease from 1.7 volt to 0.4 volt, while the output of second surface sensor 23 increases from −1.5 volt to 0.8 volt.

Comparing curves 61 and 62, it will be seen that the characteristic output curve changes with increasing thickness in that the back slope shifts to the left. Therefore the output of second surface sensor 23 will increase with greater thickness, the extent of such increase being influenced by the probe-to-first surface distance. Thus, the second surface sensor relative output yields increasingly greater differences for a fixed change in thickness as the first surface 11 moves further from probe 20. Accordingly, the output of first surface sensor 26 can be used in effect as a gain adjustment of the output of second surface sensor 23 as first surface 11 moves dynamically with respect to probe 20.

In general, measurements of the locations of the nearer and farther wall surfaces can be made by obtaining output readings from the two fiber optic sensors, and correlating these signals with probe-to-wall distance values using look-up-tables or the like in electronics 100.

The inspection technique of the preferred embodiment relies on the fact that the optics and fibre-bundles-to-lens distances are calibrated to fixed focal points, enabling the operator to set up probe 20 with respect to container wall 5. Wall 5 must be located so that it will always rotate between the focal points and such that any out-of-roundness or variations in wall thickness will not isolate these tolerances. Furthermore, additional "null clearance" (FIG. 4) should be allowed so that these variances never extend beyond the peaks 64 and 65 of respective curves 60 and 61.

Figure 5:
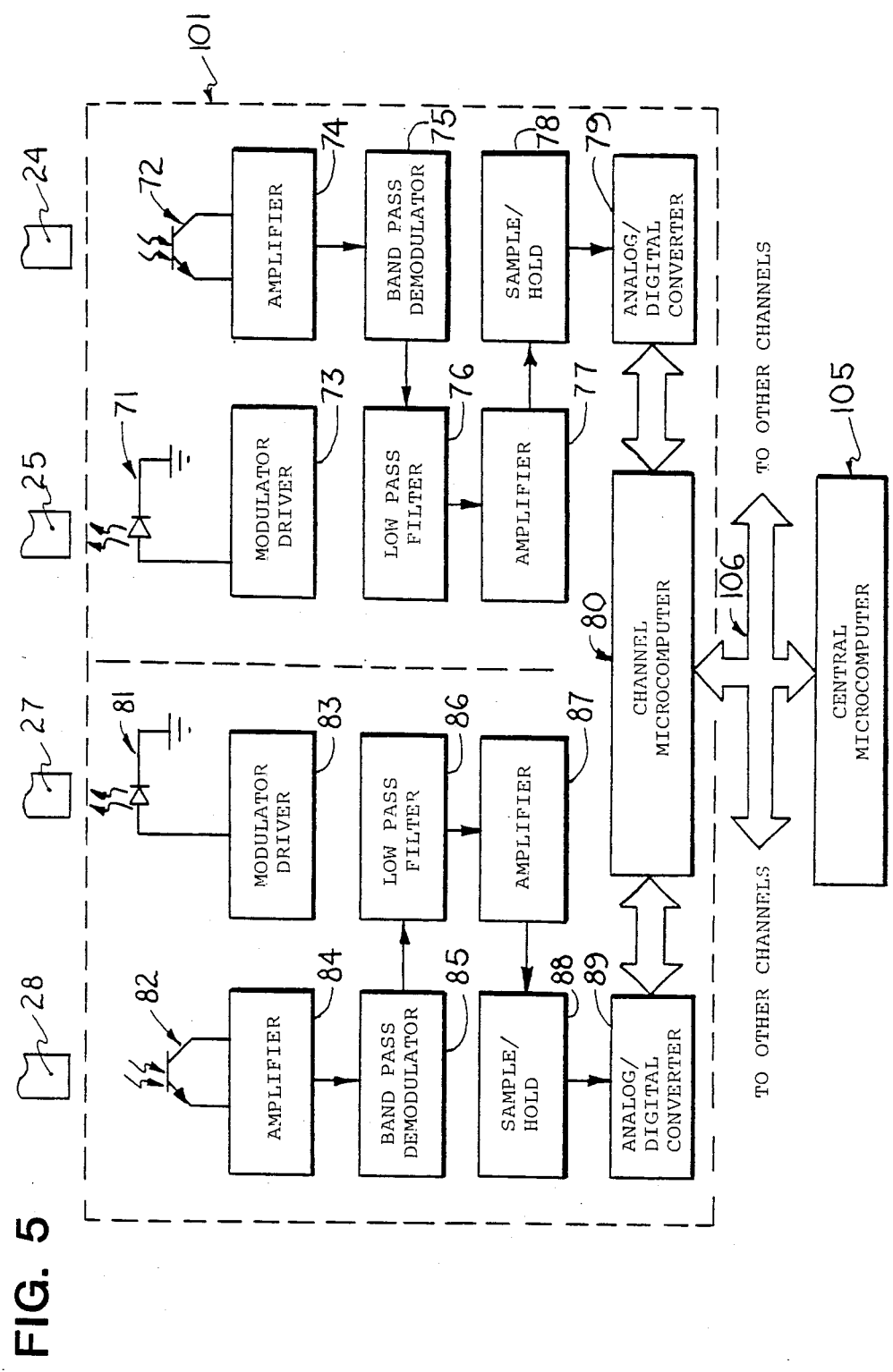
FIG. 5 is a block schematic diagram of a given channel from signal processing electronics of FIG. 1.

FIG. 5 schematically illustrates a set of components 101 for a given channel of the signal processing electronics of FIG. 1. It will be seen that each channel comprises a duplicated set of components (here shown separated by a dotted vertical line) respectively associated with fiber optic bundles 24, 25 and 27, 28.

In the illustrated embodiment the light sources for transmitting fibers 24 and 27 are respective infrared LED's 71, 81 with modulator drivers 73, 83. Infrared LED's have favorable characteristics in the illumination of flint glass as they have narrow spectral bandwidths of suitable wavelengths. In addition, these devices may be modulated at different frequencies, and provide a continuous, high intensity output with minimal drift, over a prolonged service life. LED's 71 and 81 are modulated at different frequencies to minimize spurious signals due to ambient reflections, and to reduce cross-talk between the first and second surface reflections. It should be understood that other light sources may be employed, taking into account the optical characteristics of the translucent material 15.

The illustrated photoreceivers 72, 82 are phototransistor devices which are matched in spectral response to infrared LED's 71, 81. The phototransistor outputs are demodulated by bandpass filters 75, 85 each calibrated to pass the modulation frequency of the respective infrared LED. Low pass filters 76, 86 extract the slope signals from the modulated carrier signals, which slope signals are amplified at 77, 87. The amplified slope signals are fed to sample/hold circuits 78, 88 and thence to analog-to-digital converters 79, 89, which integrate and digitalize these signals for each sample point.

A channel microcomputer 80 analyzes the integrated slope signals from both subcircuits as they are compiled for rotating container 5. Channel microcomputer 80 carries out the following functions:

(1) calculates wall thickness at each point reading
(2) controls A/Ds 79, 89 and S/Hs 78, 88
(3) assigns an automatic gain (100% peak value for output curves) for each inspection
(4) calculates and displays various significant data such as the minimum and maximum thickness values for each cycle, the number of samplings for each inspection, the degrees of resolution per cycle, and (for concentricity inspection) the minimum and maximum diameter
(5) outputs reject commands when detected values fall outside acceptable limits.

The automatic gain (item 3) is calculated as the transparent article enters the inspection station, at which time its sidewall is monitored to determine the output peaks. The sampling rate, resolution, and other parameters are a function of the electronic components together with the motion of the article relative to the scanning heads, as will be apparent to the person of ordinary skill in the art. The microcomputer may also carry out further analysis such as seam identification, and may implement software filtering to eliminate spurious signals due to wall inclusions (stones, blisters, etc.) which might cause fluke reflections. An averaging algorithm as well known in the art may be used to smooth out harmonic signal variations due to vibration of the article-rotating mechanism.

Figure 6:
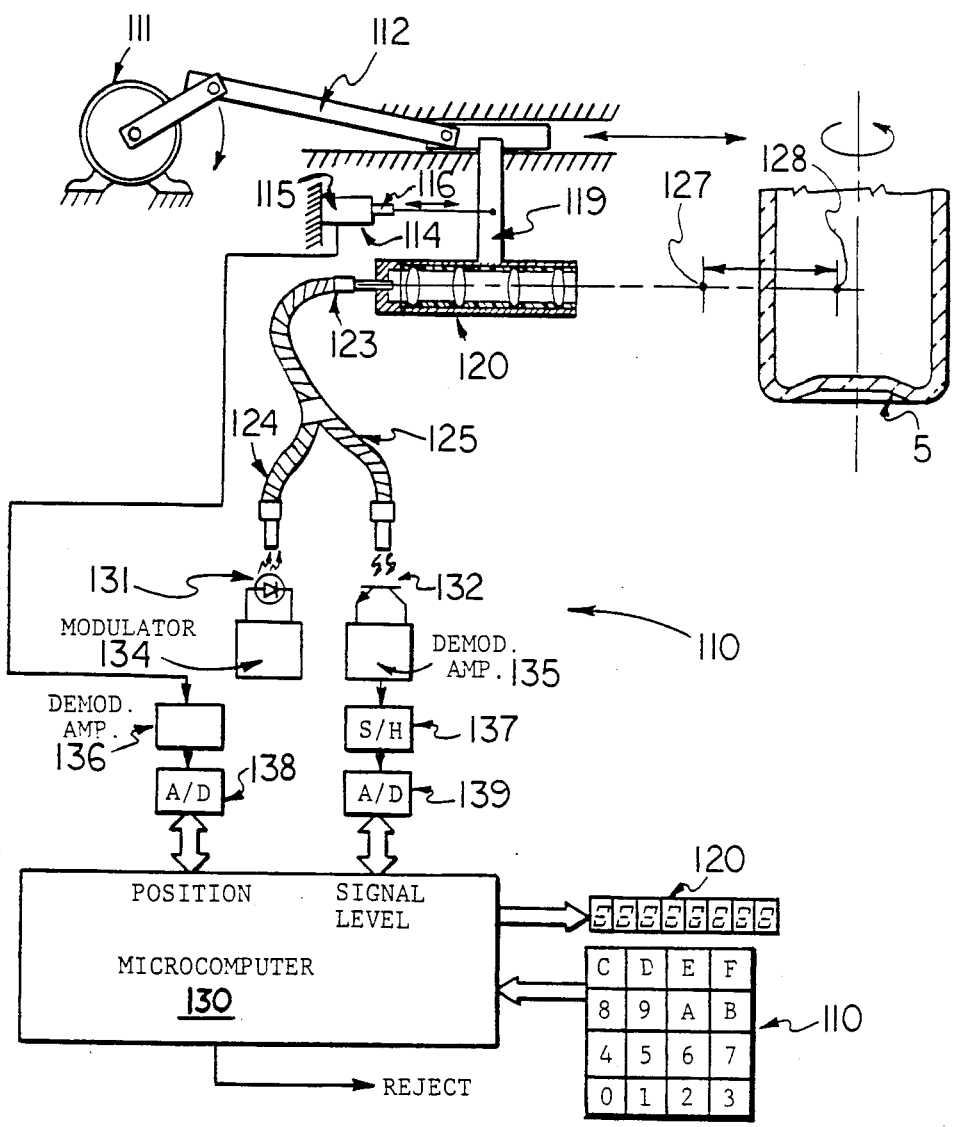
FIG. 6 is a somewhat schematic view of inspection apparatus in an alternative embodiment of the invention.

An alternative embodiment of invention, schematically illustrated in FIG. 6, uses one or more probes 120 each including a single bifurcated bundle 123. Probe 120 is caused to reciprocate in direction S-S (i.e. essentially parallel to the scanning axis) relative to the transparent container 5. In the illustrated embodiment this is achieved by reciprocating slider assembly 112 using motor 111 while rotating container 5 around its axis of symmetry, slider assembly being linked to scanning head 120 by arm 117.

With reference to FIG. 2, the inspection technique of FIG. 6 entails measuring the difference in probe-to-target distance between null points 43 and 45, relying on the fact that each null occurs when the image is focused on one of the respective wall surfaces 11, 13. This difference is used to derive the wall thickness, taking into account that the surface 13 appears to be closer to the optics due to the index of refraction of the transparent material, via the formula:

$$\frac{S^1}{S} = \frac{N^1}{N}$$

where:
$S^1$ = virtual image distance
$S$ = actual image distance
$N^1$ = index of refraction of viewing medium (typically air)
$N$ = index of refraction of image medium.

A slight adjustment based on the light transmission characteristics of medium 15 may be necessary, to compensate for shifts in null position over varying wall thicknesses.

In the apparatus of FIG. 6, the signal processing electronics generates an analog signal at the first and second nulls as the scanning head 120 is cycled toward and away from the container wall. As each of the nulls occur, it is correlated with a relative position of the probe 120; the cycling of probe 120 should be at a high speed relative to the rotation of container 5 so that the container wall appears to be essentially stationary to the moving probe. A variety of position transducers may be employed to track probe 120. The illustrated apparatus utilizes a linear variable differential (LVDT) 114, which generates an analog signal proportional to the displacement of core 116 relative to coil 115. The output signal of LVDT 114 is processed via demodulator/amplifier 136 and analog to digital converter 138 to provide a digital probe position signal to microcomputer 130. This signal is correlated by microcomputer 130 with the "signal level" (or relative intensity) signal representative of light collected by phototransistor 132 and processed by components 135, 137, and 139. Microcomputer 130 can simply monitor null occurrences and simultaneously log the probe position at each null occurrence.

An alternative position transducer, not shown in FIG. 6, is a shaft encoder coupled to the shaft of motor 111.

In an alternative mechanical arrangement, the probe 120 would be maintained stationary, while the focal point of the optics is reciprocated over the desired interval by a light weight moving optics package. This alternative arrangement would reduce the mass of the moving components and allow better resolution due to higher cycling speeds.

As mentioned above, the inspection techniques of the invention are applicable not only to measuring the thickness of a transparent wall, but also to measuring shifts in wall position such as occur in "out of round" containers. For example, the apparatus of FIGS. 1, 3, 5 might compile a set of surface displacement readings over the entire circumference of container 5. Microprocessor 80 (FIG. 5) could calculate an average value for the displacement from container to probe, as well as maximum and minimum deviations from this average. These min/max deviation values could be compared to preset values to reject containers falling outside the acceptable range.

While reference has been made above to specific embodiments, it will be apparent to those skilled in the art that various modifications and alterations may be made thereto without departing from the spirit of the present invention. For example, the inspection technique of the insertion may be easily adapted to monitoring the thickness and flatness of plate glass, transparent plastic sheets, etc., using scanning heads directed at one face. Therefore, it is intended that the scope of this invention be ascertained by reference to the following claims.

We claim:

1. Apparatus for inspecting transparent layers, comprising:
   a scanning head, comprised of first and second bifurcated fiber optic bundles each including sender and receiver bifurcations respectively containing sender and receiver optical fibers, and a joined portion containing said sender and receiver fibers terminating at a probe end; a light source for illuminating the sender fibers; a lens system for transmitting light emitted from the sender fibers at said probe end toward said transparent layer, said layer having nearer and farther surfaces, and for transmitting light reflected by said transparent layer toward said probe ends; wherein said pair of fiber optic bundles are displaced at different distances from said lens system;
   means for each of said fiber optic bundles for producing output signals essentially representative of the intensity of light transmitted by the respective receiver fibers; and
   processing means for deriving the locations of the nearer and further surfaces from said output signals.

2. Apparatus as defined in claim 1, wherein light emitted by said first and second fiber optic bundles is focused by said lens system at different first and second focal lengths, and wherein during inspection the transparent layer is placed between said first and second focal lengths relative to said scanning head.

3. Apparatus as defined in claim 1, wherein said processing mean includes memory means containing, for both the first and second container surfaces, values of surface location correlated with output signal values.

4. Apparatus as defined in claim 1, for detecting wall thickness, wherein said processing means further calculates the separation of said nearer and farther surface locations.

5. Apparatus as defined in claim 1, for providing a circumferential inspection of transparent containers, further comprising means for causing the relative motion of said container and said scanning head wherein said scanning head circumferentially scans said container.

6. Apparatus as defined in claim 5, for measuring the concentricity of container walls relative to an axis of symmetry of said container, wherein said processing means further calculates variations in diameter of the container wall.

7. Apparatus as defined in claim 5, comprising a plurality of scanning heads placed at different axial locations relative to an axis of symmetry of said container.

8. Apparatus as defined in claim 1, wherein said fiber optic bundles each include approximately equal numbers of sender and receiver fibers, which are intermingled at the probe end of said bundle.

9. Apparatus as defined in claim 1, wherein the light sources for said first and second fiber optic bundles provide amplitude-modulated light at different frequencies, and the respective processing means includes a photodetector device for producing a light intensity output signal, and means for demodulating the light intensity output signal of the respective photodetector device.

10. Apparatus as defined in claim 1, wherein the processing means provides a plurality of output signals over respective sampling intervals, and includes means for producing instantaneous intensity signals, and means for integrating the instantaneous intensity signals over the respective sampling intervals.

11. Apparatus for inspecting transparent layers, comprising:
    a fiber optic probe comprising a bifurcated fiber optic bundle including sender and receiver bifurcations respectively containing sender and receiver optical fibers, and a joined portion containing said sender and receiver fibers terminating at a probe end, further comprising a light source for illuminating the sender fibers, a lens assembly for transmitting light emitted by the sender fibers at the probe end toward said transparent layer and a photodetector means for producing an electrical output signal representative of the intensity of light transmitted by said receiver fibers;
    means for reciprocating the fiber optic probe relative to the transparent layer;
    position sensing means for producing position signals essentially representative of the instantaneous position of the fiber optic probe relative to the layer; and
    means for sensing first and second peak values of a relative intensity signal derived from said electrical output signal, and for correlating said peak values with said position signals to produce output signals representing the locations of nearer and farther surfaces of the layer.

12. Apparatus as defined in claim 11 for inspecting transparent container walls, wherein the transparent container rotates around an axis of symmetry during inspection, and wherein the fiber optic probe reciprocates relative to the container at a high rate with respect to the speed of rotation of said container.

13. Apparatus as defined in claim 11 wherein the reciprocating means comprises a motor with a motor shaft, and a sliding crank linkage interconnecting said motor shaft with said fiber optic probe.

14. Apparatus as defined in claim 11 wherein the position sensing means comprises a shaft encoder for sensing the angular rotation of the shaft of said motor.

15. Apparatus as defined in claim 11 wherein the position sensing means comprises an LVDT coupled to said fiber optic probe.

16. Apparatus as defined in claim 11, wherein the sensing and correlating means produces output signals over a plurality of sampling intervals by integrating of the relative intensity signals.

17. Apparatus for inspecting transparent layers, comprising:
    a fiber optic probe having first and second fiber optic bundles with sender and receiver fibers in each of said bundles terminating at a probe end, and a light source for each of said bundles illuminating the sender fibers to transmit light toward the transparent layer;

a lens system located between the fiber optic bundles and the transparent layer, said first and second fiber optic bundles and said lens system being adapted to transmit from the first and second bundles light which fouses at two field straddling the tranparent layer;

photodetector means coupled to said receiver fibers of each bundle for detecting light reflected by nearer and farther surfaces of the transparent layer and received by said receiver fibers at the probe end, and producing relative intensity signals indicative of the intensity of the detected light; and means for processing said relative intensity signals to derive the positions of the nearer and farther surface relative to the fiber optic probe.

18. Apparatus for inspecting tranparent layers, comprising:

a fiber optic probe having sender and receiver fibers terminating at a probe end, with a light source for illuminating the sender fibers to transmit light toward the transparent layer;

a photodetector for detecting light reflected by nearer and farther surfaces of the transparent layer and received by said receiver fibers at the probe end, and for producing relative intensity signals indicative of the intensity of the detected light; and means for processing the relative intensity signals to derive the positions of the nearer and farther surfaces relative to the fiber optic probe, said processing means including memory means for storing a plurality of relative intensity values correlated with relative position values.

19. Apparatus for inspecting transparent layers, comprising:

a fiber optic probe having sender and receiver fibers terminating at a probe end, with a light source for illuminating the sender fibers to transmit light toward the transparent layer;

a photodetector for detecting light reflected by nearer and farther surfaces of the transparent layer and received by said receiver fibers at the probe end, and for producing relative intensity signals indicative of the intensity of the detected light;

means for reciprocating said fiber optic probe relative to said transparent layer;

means for monitoring the motion of the fiber optic probe and producing probe position output signals indicative thereof; and means for processing the relative intensity signals to derive the positions of the nearer and farther surfaces relative to the fiber optic probe by correlating nulls in the relative intensity signals with said probe position output signals.

* * * * *